(12) United States Patent
Wynn et al.

(10) Patent No.: US 8,623,926 B2
(45) Date of Patent: Jan. 7, 2014

(54) PROCESS FOR THE PRODUCTION OF METHANOL INCLUDING TWO MEMBRANE SEPARATION STEPS

(75) Inventors: Nicholas P Wynn, Redwood City, CA (US); Sylvie Thomas-Droz, Mountain View, CA (US); Meijuan Zhou, Fremont, CA (US); Zhenjie He, Fremont, CA (US); Haiqing Lin, Mountain View, CA (US)

(73) Assignee: Membrane Technology and Research, Inc., Newark, CA (US)

( * ) Notice: Subject to any disclaimer, the term of this patent is extended or adjusted under 35 U.S.C. 154(b) by 77 days.

(21) Appl. No.: 13/446,677

(22) Filed: Apr. 13, 2012

(65) Prior Publication Data

US 2013/0005840 A1     Jan. 3, 2013

Related U.S. Application Data

(63) Continuation-in-part of application No. 13/175,399, filed on Jul. 1, 2011, now Pat. No. 8,168,685.

(51) Int. Cl.
*C07C 27/00*     (2006.01)
(52) U.S. Cl.
USPC .................................................. 518/700
(58) Field of Classification Search
USPC .................................................. 518/700
See application file for complete search history.

(56) References Cited

U.S. PATENT DOCUMENTS

| 1,569,775 A | 1/1926 | Mittasch et al. |
| 4,963,165 A | 10/1990 | Blume et al. |
| 5,034,126 A | 7/1991 | Reddy et al. |

OTHER PUBLICATIONS

K. O'Brien et al. "Fabrication and Scale-Up of PBI-based Membrane System for Pre-Combustion Capture of Carbon Dioxide," DOE NETL Project Fact Sheet, 2009.
B. T. Low et al., "Simultaneous Occurrence of Chemical Grafting, Cross-linking, and Etching on the Surface of Polyimide Membranes and Their Impact on H2/CO2 Separation," Macromolecules, vol. 41, No. 4, pp. 1297-1309, 2008.
Lin et al., "Materials selection guidelines for membranes that remove CO2 from gas mixtures," J. Mol. Struct., 739, 57-75, 2005.
Lin et al., "Plastization-Enhanced Hydrogen Purification Using Polymeric Membranes," Science, 311, 639-642, 2006.

*Primary Examiner* — Jafar Parsa
(74) *Attorney, Agent, or Firm* — J. Farrant

(57) ABSTRACT

Disclosed herein is a methanol production process that includes at least two membrane separation steps. Using the process of the invention, the efficiency of methanol production from syngas is increased by reducing the compression requirements of the process and/or improving the methanol product yield. As an additional advantage, the first membrane separation step generates a hydrogen-rich stream which can be sent for other uses. An additional benefit is that the process of the invention may debottleneck existing methanol plants if more syngas or carbon dioxide is available, allowing for feed of imported carbon dioxide into the synthesis loop. This is a way of sequestering carbon dioxide.

12 Claims, 2 Drawing Sheets

(not in accordance with the invention)

PROCESS FOR THE PRODUCTION OF METHANOL INCLUDING TWO MEMBRANE SEPARATION STEPS

RELATED APPLICATIONS

This application claims the benefit of U.S. application Ser. No. 13/175,399, filed Jul. 15, 2011, the disclosure of which is hereby incorporated herein by reference in its entirety.

FIELD OF THE INVENTION

The invention relates to a methanol production process that includes at least two membrane separation steps, using a hydrogen-selective membrane followed by a carbon dioxide-selective membrane, to improve the efficiency of methanol production from natural gas. Hydrogen recovered during the membrane separation step can be sent for other uses. The process of the invention may debottleneck existing methanol plants, allowing for feed of recycled carbon dioxide into the synthesis loop, resulting in sequestration of the carbon dioxide and production of additional methanol.

BACKGROUND OF THE INVENTION

Methanol, the simplest alcohol, with a chemical formula of $CH_3OH$, is a light, volatile, colorless, flammable liquid. A polar liquid at room temperature, methanol finds use as an antifreeze, solvent, fuel, and as a denaturant for ethanol. It is also used for producing biodiesel via a transesterification reaction.

The largest use of methanol, however, is in the manufacture of other chemicals. About forty percent of methanol is converted to formaldehyde, and from there into products as diverse as plastics, plywood, paints, explosives, and permanent-press textiles.

Methanol is also used on a limited basis as fuel for internal combustion engines. The use of methanol as a motor fuel received attention during the oil crises of the 1970's due to its availability, low cost, and environmental benefits. However, due to the rising cost of methanol and its corrosivity to rubber and many synthetic polymers used in the auto industry, by the late 1990s automakers had stopped building vehicles capable of operating on either methanol or gasoline ("flexible fuel vehicles"), switching their attention instead to ethanol-fueled vehicles. Even so, pure methanol is required as fuel by various auto, truck, and motorcycle racing organizations.

In 1923, German chemists Alwin Mittasch and Mathias Pier, working for BASF, developed a process for converting synthesis gas (a mixture of carbon monoxide, carbon dioxide, and hydrogen) into methanol. The process used a chromium and magnesium oxide catalyst and required extremely vigorous conditions—pressures ranging from 50 to 220 bar, and temperatures up to 450° C. A patent (U.S. Pat. No. 1,569,775) covering this process was issued on Jan. 12, 1926.

Modern methanol production has been made more efficient through the use of catalysts (typically copper) capable of operating at lower pressures. The modern low-pressure methanol (LPM) production process was developed by ICI in the late 1960's, with the technology now owned by Johnson Matthey (London), a leading licensor of methanol technology.

The production of synthesis gas ("syngas") via steam reforming of natural gas is the first step in many processes for methanol production. At low to moderate pressures and at high temperatures around 850° C., methane reacts with steam on a nickel catalyst to produce syngas according to the following reactions:

$$CH_4 + H_2O \rightarrow CO + 3H_2$$
$$CO + H_2O \rightarrow CO_2 + H_2$$

This process, commonly referred to as "steam methane reforming" (SMR) is highly endothermic, and maintaining reaction temperature by external heating is a critical part of the process.

The syngas is then compressed and reacted on a second catalyst to produce methanol. Today, the most commonly used catalyst is a mixture of copper, zinc oxide, and alumina first used by ICI in 1966. At 50-100 bar and 250° C., it can catalyze the production of methanol from syngas with high selectivity:

$$CO + 2H_2 \rightarrow CH_3OH$$
$$CO_2 + 3H_2 \rightarrow CH_3OH + H_2O$$

The production of syngas from methane produces 3 moles of hydrogen gas for every mole of carbon monoxide (and 4 moles of hydrogen per mole of carbon dioxide), while the methanol synthesis reaction consumes only 2 moles of hydrogen gas per mole of carbon monoxide (and 3 moles of hydrogen gas per mole of carbon dioxide). In both reaction pathways, one more mole of hydrogen is generated than is needed for methanol synthesis. This excess hydrogen occupies capacity in both the compressor train and the methanol reactor. As a result, the methanol production process is inefficient, resulting in unnecessary costs due to increased compressor power requirements and less than optimum methanol yields. Reactants are lost when excess hydrogen is purged from the synthesis loop and used as fuel for the reformer.

FIG. 1 is a schematic showing a conventional process for methanol production. Feed streams of natural gas 101 and steam 102 are fed into reformer 103, resulting in the production of syngas stream 104. Syngas stream 104 is then passed to compression chain 105 (typically comprising at least make-up compressor 105a and recycle compressor 105b) to produce high-pressure gas stream 106. High-pressure stream 106 is then passed to methanol synthesis reactor 107 to produce reaction product stream 108, containing methanol and unreacted syngas. This stream 108 is then routed to condenser 109, from which condensed stream 110, containing methanol and water, drops out. Overhead stream 111, containing unreacted syngas and enriched in hydrogen and inerts (methane and possibly nitrogen), is then split into purge stream 112 and recycle stream 113, which is routed back to the recycle compressor 105b, where it is combined with fresh feed.

It would be desirable to provide an improved methanol production process that is more efficient, with reduced compressor power requirements and/or improved methanol product yield.

SUMMARY OF THE INVENTION

In our earlier application, U.S. Ser. No. 13/175,399, filed Jul. 15, 2011, which has been allowed, we disclosed processes for the production of methanol from syngas which removed excess hydrogen from the syngas before it reaches the methanol synthesis loop.

We have since discovered an even more efficient process, in which excess hydrogen is removed after the methanol synthesis loop, and carbon dioxide is recycled back to the synthesis loop.

Accordingly, disclosed herein is a methanol production process including the following steps:

(a) providing a source of syngas, wherein the syngas has a first composition parameter $R_1$, where $R_1 > 2$;

(b) passing the syngas to a methanol synthesis loop to produce a condensed methanol product stream;

(c) withdrawing a purge stream from the methanol synthesis loop to limit the concentration of inerts and excess hydrogen;

(d) providing a first membrane having a first feed side and a first permeate side, where the first membrane exhibits a selectivity to hydrogen over carbon dioxide of at least about 5, and a selectivity to hydrogen over carbon monoxide of at least about 20;

(e) passing at least a portion of the purge stream across the first feed side;

(f) withdrawing from the first permeate side a hydrogen-rich first permeate stream, wherein the first permeate stream has a second composition parameter $R_2$, where $R_2<R_1$;

(g) withdrawing from the first feed side a hydrogen-depleted first residue stream;

(h) providing a second membrane having a second feed side and a second permeate side, where the second membrane is selective for carbon dioxide over hydrogen and methane;

(i) passing the first residue stream across the second feed side;

(j) withdrawing from the second feed side a carbon dioxide-depleted second residue stream;

(k) withdrawing from the second permeate side a carbon dioxide-enriched second permeate stream, wherein the second permeate stream has a third composition parameter $R_3$, where $R_3<R_2$; and (l) passing the second permeate stream to the methanol synthesis loop.

Membranes for use in the first membrane separation step (d) preferably exhibit a selectivity to hydrogen over carbon dioxide of at least about 5 and, more preferably, at least about 10, and to hydrogen over carbon monoxide of at least about 20. Hydrogen permeance of the first membrane is typically at least 100 gpu and, preferably, at least 200 gpu.

Preferred first membrane materials include polymers, such as polyimides, polyamides, polyurethanes, polyureas, polybenzimidazoles, and polybenzoxazoles; metals, such as palladium; zeolites; and carbon, by way of example and not by way of limitation.

First membrane operating temperature is typically within the range of about 50° C. to about 150° C.; preferably, within the range of about 100° C. to about 150° C. The feed side of the first membrane is typically maintained at a pressure within the range of about 45 bar to about 100 bar, with the permeate side typically maintained at a pressure within the range of about 2 bar to about 10 bar.

Any membrane that exhibits a selectivity to carbon dioxide over hydrogen of at least about 5, and over methane of at least about 10, may be used in the second membrane separation step (h). Carbon dioxide permeance of the second membrane is typically at least 200 gpu and, preferably, at least 400 gpu.

Any membrane with suitable performance properties may be used in second membrane separation step (h). Many polymeric materials, especially elastomeric materials, are very permeable to carbon dioxide. Preferred membranes for separating carbon dioxide from other gases often have a selective layer based on a polyether.

Second membrane operating temperature is typically within the range of about 0° C. to about 80° C.; preferably, within the range of about 20° C. to about 60° C. The feed side of the second membrane is typically maintained at a pressure within the range of about 45 bar to about 100 bar, with the permeate side typically maintained at a pressure within the range of about 10 bar to about 30 bar.

By practicing the process of the invention, existing methanol plants may be made more efficient by recovering carbon dioxide from the purge gas and recycling it back to the synthesis loop. This results in additional methanol production, and is also a way of sequestering carbon dioxide, thereby preventing its release to the environment. In addition, the process of the invention generates a hydrogen-rich stream from the first membrane separation step. This hydrogen-rich stream can be used for other purposes.

DETAILED DESCRIPTION OF THE INVENTION

The terms "natural gas" and "methane" are used interchangeably herein.

Gas percentages given herein are by volume unless stated otherwise.

Pressures as given herein are in bar absolute unless stated otherwise.

For any gas stream herein, the composition may be expressed in terms of a composition parameter, R, where:

$$R = \frac{(\text{molar flow of } H_2 - \text{molar flow of } CO_2)}{(\text{molar flow of } CO + \text{molar flow of } CO_2)},$$

Specific composition parameters are referred to herein as $R_1$, $R_2$, and $R_3$.

Figure 1:
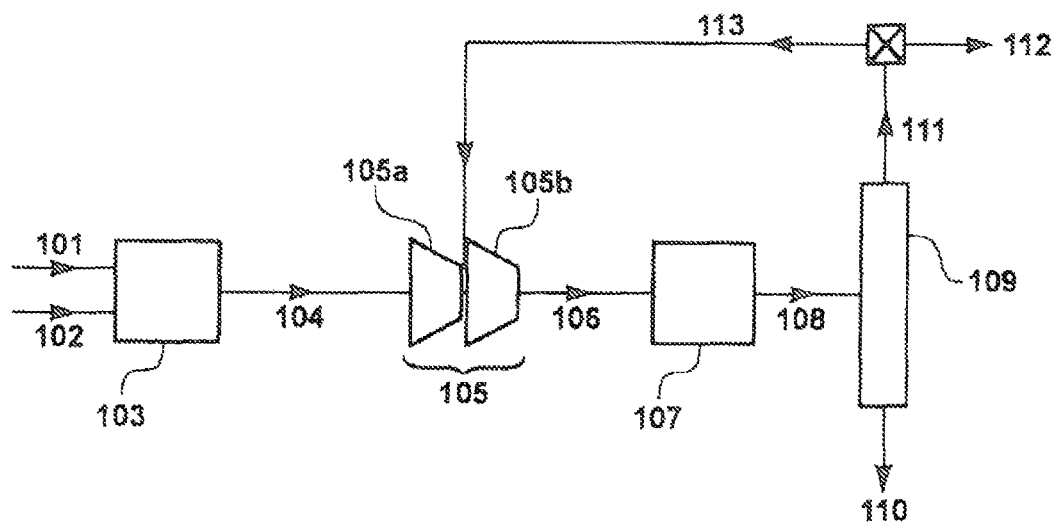
FIG. 1 is a schematic drawing of a conventional methanol production process (not in accordance with the invention).
Figure 2:
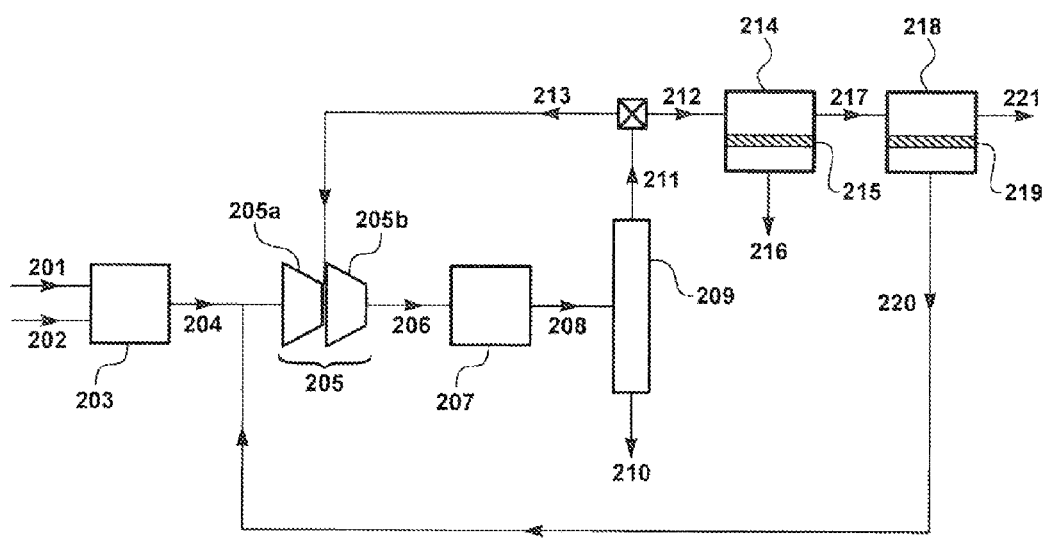
FIG. 2 is a schematic drawing of a basic embodiment process of the invention for methanol production that involves two membrane separation steps to treat a purge stream from the methanol production process.

A schematic drawing of a basic embodiment process of the invention for methanol production is shown in FIG. 2. It will be appreciated by those of skill in the art that this, like FIG. 1, is a very simple block diagram, intended to make clear the key unit operations of the process of the invention, and that an actual process train will usually include many additional steps of a standard type, such as heating, chilling, compressing, condensing, pumping, various types of separation and/or fractionation, as well as monitoring of pressures, temperatures, flows, and the like. It will also be appreciated by those of skill in the art that the details of the unit operations may differ from product to product.

Referring to the figure, feed streams of natural gas, 201, and steam, 202, are fed into, for example, a steam reformer, 203, resulting in the production of syngas, 204. Although FIG. 2 illustrates an example in which syngas is produced using a steam methane reforming process, any source of syngas can be used to provide syngas for use in the process of the invention.

The invention is particularly designed for syngas sources having an excess of hydrogen for methanol production. Expressed quantitatively, the invention is particularly directed to the manufacture of methanol from syngas having a composition parameter, $R_1$, that is greater than 2; that is, $R=R_1>2$.

Syngas stream 204 is then passed to a compression chain, 205 (typically comprising at least a make-up compressor, 205a, and a recycle compressor, 205b), to produce a high-pressure gas stream, 206. High-pressure stream 206 is then passed to a methanol synthesis reactor, 207, to produce a reaction product stream, 208, containing methanol and unreacted syngas.

Methanol synthesis reactors are known in the art and typically rely on a catalyst bed to catalyze the reaction of carbon oxides and hydrogen to produce methanol. As discussed in the Background of the Invention, the most common catalyst in use today is a mixture of copper, zinc oxide, and alumina first used by ICI in 1966. At 50-100 bar and 250° C., it can catalyze the production of methanol from carbon oxides and hydrogen with high selectivity.

Reaction product stream 208 is then routed to a condenser, 209, from which a condensed stream, 210, containing methanol and water, drops out. An overhead stream, 211, containing unreacted syngas and enriched in hydrogen and inerts (methane and possibly nitrogen), is then split into a purge stream, 212, and a recycle stream, 213, which is routed back to the recycle compressor 205b, where it is combined with fresh feed.

In accordance with the present invention, at least a portion of purge stream 212 is then passed as a feed stream to a first membrane unit, 214, that includes membranes, 215, that exhibit a selectivity to hydrogen over carbon dioxide of at least about 5; preferably, at least about 10; more preferably, at least about 15. In addition, the membranes 215 should exhibit a selectivity for hydrogen over carbon monoxide of at least about 20. Hydrogen permeance of the first membrane is typically at least 100 gpu and, preferably, at least 200 gpu.

Any membrane with suitable performance properties may be used in the first membrane separation step. Examples of such membranes include the polybenzimidazole (PBI) based membranes taught by K. O'Brien et al. in "Fabrication and Scale-Up of PBI-based Membrane System for Pre-Combustion Capture of Carbon Dioxide" (DOE NETL Project Fact Sheet 2009) and polyimide-based membranes taught by B. T. Low et al. in "Simultaneous Occurrence of Chemical Grafting, Cross-linking, and Etching on the Surface of Polyimide Membranes and Their Impact on $H_2/CO_2$ Separation" (*Macromolecules*, Vol. 41, No. 4, pp. 1297-1309, 2008).

Preferred first membrane materials include polymers, such as polyimides, polyamides, polyurethanes, polyureas, polybenzimidazoles, and polybenzoxazoles; metals, such as palladium; zeolites; and carbon, by way of example and not by way of limitation.

The membrane may take the form of a homogeneous film, an integral asymmetric membrane, a multilayer composite membrane, a membrane incorporating a gel or liquid layer or particulates, or any other form known in the art.

The membranes may be manufactured as flat sheets or as fibers and housed in any convenient module form, including spiral-wound modules, plate-and-frame modules, and potted hollow-fiber modules. The making of all these types of membranes and modules is well-known in the art.

Flat-sheet membranes in spiral-wound modules is the most preferred choice for the membrane/module configuration. A number of designs that enable spiral-wound modules to be used in counterflow mode, with or without sweep on the permeate side, have been devised. A representative example is described in U.S. Pat. No. 5,034,126, to Dow Chemical.

Membrane unit 214 may contain a single membrane module or bank of membrane modules or an array of modules. A single unit or stage containing one or a bank of membrane modules is adequate for many applications. If the residue stream requires further hydrogen removal, it may be passed to a second bank of membrane modules for a second processing step. If the permeate stream requires further concentration, it may be passed to a second bank of membrane modules for a second-stage treatment. Such multi-stage or multi-step processes, and variants thereof, will be familiar to those of skill in the art, who will appreciate that the membrane separation step may be configured in many possible ways, including single-stage, multistage, multistep, or more complicated arrays of two or more units, in serial or cascade arrangements.

The first membrane operating temperature is typically within the range of about 50° C. to about 150° C.; preferably, within the range of about 100° C. to about 150° C. The feed side of the first membrane is typically maintained at a pressure within the range of about 45 bar to about 100 bar, with the permeate side typically maintained at a pressure within the range of about 2 bar to about 10 bar.

Referring back to FIG. 2, purge stream 212 is passed across the feed side of the membranes 215. A permeate stream, 216, is withdrawn from the permeate side. Permeate stream 216 is enriched in hydrogen as compared with purge stream 212, and has a composition parameter $R_2$, where $R_2 > R_1$.

Hydrogen-rich stream 216 can be used for whatever purpose is desired. It may, for example, be used as reformer fuel gas, or used as a source of hydrogen for another process, such as ammonia production.

A hydrogen-depleted first residue stream, 217, is withdrawn from the feed side of first membrane unit 214. First residue stream 217 is then routed to a second membrane separation unit, 218. Second membrane separation unit 218 includes membranes, 219, that are selective for carbon dioxide over hydrogen, methane, and nitrogen.

In particular, the membranes in second unit 218 typically have a selectivity for carbon dioxide over hydrogen of at least about 5; over methane of at least about 10; and, over nitrogen of at least about 20. Carbon dioxide permeance of the second membrane is typically at least 200 gpu and, preferably, at least 400 gpu.

Any membrane with suitable performance properties may be used in the second membrane separation step. Many polymeric materials, especially elastomeric materials, are very permeable to carbon dioxide. Such polymeric materials are described, for example, in two publications by Lin et al., "Materials selection guidelines for membranes that remove $CO_2$ from gas mixtures" (*J. Mol. Struct.*, 739, 57-75, 2005) and "Plastization-Enhanced Hydrogen Purification Using Polymeric Membranes" (*Science*, 311, 639-642, 2006).

Preferred membranes for separating carbon dioxide from other gases often have a selective layer based on a polyether. Not many membranes are known to have high carbon dioxide/hydrogen selectivity. A representative preferred material for the selective layer is Pebax®, a polyamide-polyether block copolymer material described in detail in U.S. Pat. No. 4,963,165. We have found that membranes using Pebax® as the selective polymer can maintain a selectivity of 9, 10, or greater under process conditions.

Membrane modules are as discussed above.

The second membrane operating temperature is typically within the range of about 0° C. to about 80° C.; preferably, within the range of about 20° C. to about 60° C. The feed side of the second membrane is typically maintained at a pressure within the range of about 45 bar to about 100 bar, with the permeate side typically maintained at a pressure within the range of about 10 bar to about 30 bar.

A carbon dioxide-enriched second permeate stream, 220, is withdrawn from the permeate side of second membrane unit 218. The carbon dioxide content in second permeate stream 220 has now been built up from about 1-3 vol % in the purge stream 212, to about 7-30 vol % in permeate stream 220.

Carbon dioxide-enriched second permeate stream 220 is then recycled back to the methanol synthesis loop upstream of compression chain 205, where it joins syngas stream 204 as feed to the methanol synthesis loop. Second permeate stream 220 has a composition parameter $R_3$, where $R_3 < R_2$. The addition of carbon dioxide-enriched second permeate stream 220 to the feed stream to the methanol synthesis loop results in additional methanol production.

A carbon dioxide-depleted second residue stream, 221, is withdrawn from the membrane side of second membrane separation unit 218. This stream can then be sent for use as fuel gas or for any other desired purpose.

The invention is now further described by the following examples, which are intended to be illustrative of the invention, but are not intended to limit the scope or underlying principles in any way.

EXAMPLES

Example 1

Conventional Methanol Production Process (not in Accordance with the Invention)

The computer calculations in the following Examples were performed using a modeling program, ChemCad 5.6 (ChemStations, Inc., Houston, Tex.) containing code developed by assignee's engineering group for applications specific to assignee's processes.

The calculation for this Example was performed using the flow scheme shown in FIG. 1 and described in the Background of the Invention, above. This flow scheme does not include a membrane separation step upstream of the methanol synthesis process (not in accordance with the invention). Syngas flow was assumed to be 106 metric tons per hour (Mt/h).

The flow rates and chemical compositions of the streams in the methanol synthesis loop were calculated. The results of this calculation are shown in Table 1.

TABLE 1

| Parameter/Stream | Syngas 104 | Reactor Feed Gas 106 | Reactor Output 108 | Condensate 110 | Overhead Stream 111 | Purge Gas 112 | Recycle Gas 113 |
|---|---|---|---|---|---|---|---|
| Total Flow (Mt/h) | 106 | 185 | 185 | 92.0 | 93.4 | 14.0 | 79.4 |
| Temperature (° C.) | 150 | 65 | 280 | 40 | 40 | 40 | 40 |
| Pressure (bar) | 16.5 | 103 | 95 | 90 | 88 | 88 | 88 |
| Component (mol %) | | | | | | | |
| Hydrogen | 73.4 | 79.2 | 71.1 | 0.24 | 83.2 | 83.2 | 83.2 |
| Carbon monoxide | 14.9 | 6.6 | 0.80 | 0.01 | 0.93 | 0.93 | 0.93 |
| Carbon dioxide | 7.8 | 3.7 | 0.91 | 0.43 | 0.99 | 0.99 | 0.99 |
| Methane | 3.7 | 9.7 | 11.8 | 0.45 | 13.7 | 13.7 | 13.7 |
| Nitrogen | 0.20 | 0.54 | 0.65 | 0 | 0.76 | 0.76 | 0.76 |
| Methanol | 0 | 0.23 | 11.1 | 74.0 | 0.39 | 0.39 | 0.39 |
| Water | 0 | 0.04 | 3.7 | 24.9 | 0.06 | 0.06 | 0.0 |

In this "no membrane" example (not in accordance with the invention), approximately 96% of the carbon oxides in the syngas are converted to methanol. Most of the balance, approximately 3% of the carbon oxides in the feed syngas, is lost in the purge gas. The make-up compressor compresses 24,000 lbmol/h, with a power consumption of 29,000 hp. The recycle compressor compresses 50,000 lbmol/h, with a power consumption of 5,400 hp.

Example 2

Methanol Production Process in Accordance with the Invention

The calculation for this Example was performed using the flow scheme shown in FIG. 2 and described in the Detailed Description, above. This flow scheme includes two membrane separation steps downstream of the methanol synthesis loop.

The membranes, 215, in first membrane separation unit, 214, were assumed to have the properties shown in Table 2, at a membrane operating temperature within the range of about 50° C. and about 150° C.

TABLE 2

| Gas | Permeance (gpu)* | $H_2$/Gas Selectivity** |
|---|---|---|
| Hydrogen | 300 | — |
| Carbon monoxide | <2 | >100 |
| Carbon dioxide | 20 | 15 |
| Methane | <2 | >100 |
| Nitrogen | <2 | >100 |
| Water | 500 | 0.6 |

*Gas permeation unit; 1 gpu = 1 × 10$^{-6}$ cm$^3$(STP)/cm$^2$ · s · cmHg
Estimated, not measured The membranes, 219, in second membrane separation unit, 218**, were selective for carbon dioxide over hydrogen and were assumed to have the properties shown in Table 3, at a membrane operating temperature within the range of about 0° C. and about 40° C.

TABLE 3

| Gas | Permeance (gpu)* | $CO_2$/Gas Selectivity** |
|---|---|---|
| Carbon dioxide | 600 | — |
| Hydrogen | 60 | 10 |
| Carbon monoxide | 20 | 30 |
| Methane | 20 | 30 |
| Nitrogen | 30 | 20 |
| Water | 2000 | 0.3 |

*Gas permeation unit; 1 gpu = 1 × 10$^{-6}$ cm$^3$(STP)/cm$^2$ · s · cmHg
Estimated, not measured Syngas flow for this calculation was assumed to be 106 Mt/h. First membrane 215 area was assumed to be 1,343 m$^2$; second membrane 219** area was assumed to be 1,427 m$^2$.

The flow rates and chemical compositions of the streams in the methanol synthesis loop were calculated. The results of this calculation are shown in Table 4.

TABLE 4

| Parameter/Stream | Syngas 204 | Reactor Feed Gas 206 | Reactor Output 208 | Product Stream 210 | Overhead Stream 211 | Purge Gas 212 | Recycle Gas 213 | First Mem. Perm. 216 | Second Mem. Perm. 220 | Fuel Gas 221 |
|---|---|---|---|---|---|---|---|---|---|---|
| Total Flow (Mt/h) | 106 | 177 | 177 | 92 | 85 | 20 | 65 | 7.4 | 6.2 | 6.0 |
| Temperature (° C.) | 150 | 70 | 280 | 50 | 50 | 50 | 50 | 53 | 50 | 43 |
| Pressure (bar) | 16.5 | 103 | 95 | 90 | 88 | 86 | 86 | 2.1 | 16.5 | 103 |
| Component (mol %) | | | | | | | | | | |
| Hydrogen | 73.4 | 73.5 | 61.0 | 0.27 | 75.6 | 75.6 | 75.6 | 95.1 | 15.2 | 5.0 |
| Carbon monoxide | 14.9 | 8.2 | 1.1 | 0.01 | 1.3 | 1.3 | 1.3 | 0.20 | 4.5 | 5.5 |
| Carbon dioxide | 7.8 | 4.7 | 1.2 | 0.53 | 1.4 | 1.4 | 1.4 | 0.55 | 8.0 | 0.23 |
| Methane | 3.7 | 12.6 | 16.2 | 0.70 | 19.9 | 19.9 | 19.9 | 3.0 | 68.4 | 84.5 |
| Nitrogen | 0.2 | 0.71 | 0.91 | 0.01 | 1.1 | 1.1 | 1.1 | 0.17 | 3.4 | 4.8 |
| Methanol | 0 | 0.31 | 14.7 | 73.5 | 0.65 | 0.65 | 0.65 | 0.84 | 0.02 | 0 |
| Water | 0 | 0.05 | 4.9 | 25.0 | 0.11 | 0.11 | 0.11 | 0.14 | 0 | 0 |

In this "two membrane" example (in accordance with the invention), approximately 98% of the carbon oxides in the syngas are converted to methanol. Most of the balance, approximately 2% of the carbon oxides in the feed syngas, is lost in the purge gas. The make-up compressor compresses 24,800 lbmol/h, with a power consumption of 29,800 hp. The recycle compressor compresses 50,000 lbmol/h, with a power consumption of 5,400 hp.

We claim:

1. A process for the production of methanol comprising the following steps:
    (a) providing a source of syngas, wherein the syngas has a first composition parameter $R_1$, where $R_1 > 2$;
    (b) passing the syngas to a methanol synthesis loop to produce a condensed methanol product stream;
    (c) withdrawing a purge stream from the methanol synthesis loop to limit the concentration of inerts and excess hydrogen;
    (d) providing a first membrane having a first feed side and a first permeate side, where the first membrane exhibits a selectivity to hydrogen over carbon dioxide of at least about 5, and a selectivity to hydrogen over carbon monoxide of at least about 20;
    (e) passing at least a portion of the purge stream across the first feed side;
    (f) withdrawing from the first permeate side a hydrogen-rich first permeate stream, wherein the first permeate stream has a second composition parameter $R_2$, where $R_2 < R_1$;
    (g) withdrawing from the first feed side a hydrogen-depleted first residue stream;
    (h) providing a second membrane having a second feed side and a second permeate side, where the second membrane is selective for carbon dioxide over hydrogen and methane;
    (i) passing the first residue stream across the second feed side;
    (j) withdrawing from the second feed side a carbon dioxide-depleted second residue stream;
    (k) withdrawing from the second permeate side a carbon dioxide-enriched second permeate stream, wherein the second permeate stream has a third composition parameter $R_3$, where $R_3 < R_2$; and
    (l) passing the second permeate stream to the methanol synthesis loop.

2. A process in accordance with claim 1, wherein the first membrane exhibits a selectivity to hydrogen over carbon dioxide of at least about 5.

3. A process in accordance with claim 2, wherein the first membrane exhibits a selectivity to hydrogen over carbon dioxide of at least about 10.

4. A process in accordance with claim 1, wherein the first membrane exhibits a selectivity to hydrogen over carbon monoxide of at least about 20.

5. A process in accordance with claim 1, wherein the at least a portion of the purge stream is passed across the first feed side at a temperature within the range of about 50° C. to about 150° C.

6. A process in accordance with claim 1, wherein the first feed side is maintained at a pressure within the range of about 45 bar to about 100 bar.

7. A process in accordance with claim 1, wherein the first permeate side is maintained at a pressure within the range of about 2 bar to about 10 bar.

8. A process in accordance with claim 1, wherein the second membrane has a selectivity for carbon dioxide over hydrogen of at least about 5.

9. A process in accordance with claim 1, wherein the second membrane has a selectivity for carbon dioxide over methane of at least about 10.

10. A process in accordance with claim 1, wherein the first residue stream is passed across the second feed side at a temperature within the range of about 0° C. to about 80° C.

11. A process in accordance with claim 1, wherein the second feed side is maintained at a pressure within the range of about 45 bar to about 100 bar.

12. A process in accordance with claim 1, wherein the second permeate side is maintained at a pressure within the range of about 10 bar to about 30 bar.

* * * * *